(12) United States Patent
Le-Khac

(10) Patent No.: US 7,276,464 B2
(45) Date of Patent: *Oct. 2, 2007

(54) TITANIUM ZEOLITE CATALYSTS

(75) Inventor: Bi Le-Khac, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 465 days.

This patent is subject to a terminal disclaimer.

(21) Appl. No.: 10/870,123

(22) Filed: Jun. 17, 2004

(65) Prior Publication Data

US 2005/0283009 A1  Dec. 22, 2005

(51) Int. Cl.
*B01J 29/06* (2006.01)
*B01J 31/00* (2006.01)

(52) U.S. Cl. .............................. 502/159; 502/64; 546/1

(58) Field of Classification Search ................ 502/64, 502/159; 546/1
See application file for complete search history.

(56) References Cited

U.S. PATENT DOCUMENTS

| | | | | |
|---|---|---|---|---|
| 3,953,402 | A | 4/1976 | Kline | 260/62 |
| 4,410,501 | A | 10/1983 | Taramasso et al. | 423/326 |
| 4,690,995 | A | 9/1987 | Keskey et al. | 526/286 |
| 5,371,160 | A * | 12/1994 | Crowe et al. | 526/263 |
| 6,008,388 | A | 12/1999 | Dessau et al. | 549/531 |
| 6,037,484 | A | 3/2000 | Grey | 549/531 |
| 6,156,245 | A | 12/2000 | Takebayashi et al. | 264/4.7 |
| 6,194,591 | B1 | 2/2001 | Grey et al. | 549/533 |
| 6,403,815 | B1 | 6/2002 | Grey | 549/532 |
| 6,958,405 | B2 * | 10/2005 | Le-Khac et al. | 549/531 |

FOREIGN PATENT DOCUMENTS

WO  WO02/085513  10/2002
WO  WO03/014014  2/2003

OTHER PUBLICATIONS

P. Kumar et al., *Synlett.* (1995) 289.
S. Kobayashi et al., *Chem. Commun.* (2003) 449.
R. Akiyama et al., *Angew. Chem. Int. Ed.* 40 (2001) 3469.
K. Edler et al., *J. Chem. Soc. Chem. Commun.* (1995) 155.
W. Kim et al., *J. Polym. Sci.: C* 26 (1988) 347.
H. Nishide et al., *Makromol.Chem.* 177 (1976) 2295.
A. D'Aprano et al.; *J. Polym. Sci.: A-2* 7 (1969) 1101.
M. Donbrow, Ed., *Microcapsules and Nanoparticles in Medicine and Pharmacy* pp. 1-14.
G. Beestman, "Microencapsulation of Solid Particles" in *Controlled-Release Delivery Systems for Pesticides* (1999) H. Scher, Ed., pp. 31-54.
S. Kobayashi et al., *J. Am. Chem. Soc.* 120 (1998) 2985.
M. Iso et al., *Zairyo Gijutsu* 3 (1985) 287.
M. Yoshida et al., *J. Appl. Polym. Sci.* 89 (2003) 1966.
Y. Hu et al., *Chem. Commun.* (2002) 788.
W. Chen et al., *Tetrahedron* 58 (2002) 3889.
D. Bergbreiter et al., *Org. Letters* 2 (2000) 393.
O. Chiantore et al., *Polym. Degrad. Stab.* 67 (2000) 461.
W. Chen et al., *Chem. Commun.* (2000) 839.
C. Perego et al., *Appl. Catal A.* 221 (2001) 63.
P. Ingallina et al., *Sci. Tech. Catal.* (1994) 31.

* cited by examiner

*Primary Examiner*—Zinna N. Davis
(74) *Attorney, Agent, or Firm*—Jonathan L. Schuchardt

(57) ABSTRACT

Catalysts useful for epoxidizing olefins are disclosed. The catalysts comprise a vinylpyridine polymer and a titanium zeolite. Preferably, the vinylpyridine polymer encapsulates the titanium zeolite. The catalysts are easy to prepare and use, they are easy to recover and reuse, and they convert olefins to epoxides in good yields with high selectivity. Surprisingly, ring-opening reactions that form glycol or glycol ether by-products are minimized by using the vinylpyridine polymer-containing catalysts. The catalysts are valuable for making propylene oxide from propylene and hydrogen peroxide. Vinylpyridine polymer-encapsulated transition metals and their use to produce hydrogen peroxide from hydrogen and oxygen is also disclosed.

10 Claims, No Drawings

TITANIUM ZEOLITE CATALYSTS

FIELD OF THE INVENTION

The invention relates to catalysts useful for oxidation reactions, particularly the epoxidation of propylene to propylene oxide (PO).

BACKGROUND OF THE INVENTION

Titanium zeolites, i.e., synthetic molecular sieves that incorporate titanium atoms in a silicate framework, catalyze a wide variety of valuable oxidative organic reactions. The versatility of titanium zeolites, particularly TS-1, for arene hydroxylation, alkane oxidation, olefin epoxidation, thioether oxidation, Baeyer-Villiger oxidation reactions, and other important transformations is well known. For a review, see P. Kumar et al., *Synlett.* (1995) 289. Titanium zeolites catalyze the epoxidation of propylene with hydrogen peroxide. The hydrogen peroxide can be supplied (see, e.g., U.S. Pat. No. 6,037,484) or it can be generated "in situ" by using titanium zeolites that incorporate a transition metal, especially palladium (see U.S. Pat. No. 6,008,388 and references cited therein).

Unwanted hydrogenation of propylene to propane complicates the "in situ" epoxidation of propylene using hydrogen, oxygen, and a transition metal-containing titanium zeolite. Nitrogen compounds such as ammonium hydroxide or ammonium bromide have been added to suppress propane formation (see U.S. Pat. No. 6,008,388). Nitrogen-containing polymers were not suggested.

Another side reaction is common to olefin epoxidations with hydrogen peroxide: zeolite-promoted ring opening of the epoxide with water and/or alcohol solvents to give glycols and glycol ethers. For example, when PO is made from propylene using TS-1 as a catalyst in aqueous methanol, ring opening reactions typically limit the PO/POE (molar ratio of propylene oxide to propylene oxide plus ring-opening products that derive from PO) to about 91% at 50° C. Selectivity deteriorates as temperature increases. In addition to sacrificing valuable epoxide product, ring opening introduces impurities that must be removed. U.S. Pat. No. 6,037,484 teaches to add 2,4-lutidine or another substituted pyridine compound to the hydrogen peroxide feed to suppress ring opening. Soluble pyridines such as these must be continually replenished in any continuous process for making an epoxide. Polymers containing pyridine moieties are not suggested.

Recently, we discovered that polymer-encapsulated titanium zeolites are valuable oxidation catalysts (see, e.g., copending application Ser. No. 10/796,842, filed Mar. 9, 2004), particularly for olefin epoxidations. In particular, we found that polymer encapsulation improves catalyst filterability (an advantage for both catalyst preparation and catalyst recovery) and provides a significant improvement in selectivity to propylene oxide (from 91% to 93% PO/POE). We also found that polymer-encapsulated transition metals effectively catalyze the reaction of hydrogen and oxygen to make hydrogen peroxide (see copending application Ser. No. 10/796,810, filed Mar. 9, 2004). Vinylpyridine polymers were not disclosed.

While the pharmaceutical industry has used polymer encapsulation for years to mask taste, impart storage stability, reduce stomach irritation, target delivery, or control release of drugs, benefits of the technique for catalysis are just now being realized (for examples, see *Chem. Commun.* (2003) 449 and references cited therein; *Angew. Chem. Int. Ed.* 40 (2001) 3469; *J. Am. Chem. Soc.* 120 (1998) 2985).

In sum, the industry would benefit from improved oxidation catalysts. In particular, the industry needs olefin epoxidation catalysts that provide good selectivity while minimizing ring-opening side reactions. Catalysts that can provide good selectivity over a wide temperature range would be especially valuable. Ideally, the catalysts would be inexpensive and easy to make. Catalysts for making hydrogen peroxide directly from hydrogen and oxygen are also needed.

SUMMARY OF THE INVENTION

The invention is a catalyst useful for oxidation reactions, especially epoxidations. The catalyst comprises a vinylpyridine polymer and a titanium zeolite. Preferably, the vinylpyridine polymer encapsulates the titanium zeolite, but a simple admixture of the vinylpyridine polymer and titanium zeolite can also be used. In epoxidations with hydrogen peroxide, the catalysts provide exceptional epoxide selectivity over a wide temperature range while minimizing ring-opening side reactions. Thus, the invention includes olefin epoxidation processes performed with the catalysts. The catalysts can include a transition metal. If so, they are useful for olefin epoxidations in which hydrogen peroxide is generated "in situ" from hydrogen and oxygen. In addition, the invention includes a process in which hydrogen and oxygen react in the presence of a vinylpyridine polymer-encapsulated transition metal to produce hydrogen peroxide.

DETAILED DESCRIPTION OF THE INVENTION

Catalysts of the invention include a titanium zeolite. Titanium zeolites are well-characterized, crystalline synthetic silicates or aluminosilicates that incorporate titanium atoms in the framework. The choice of titanium zeolite used depends upon many factors, particularly the type of organic reaction that it will catalyze and the identity of the reactants. In olefin epoxidations, the choice of zeolite depends on the size and shape of the olefin to be epoxidized. It is preferred to use a relatively small pore titanium zeolite such as titanium silicalite if the olefin is a lower olefin such as ethylene, propylene, or 1-butene. When the olefin is propylene, TS-1 is particularly preferred. For a bulky olefin such as cyclohexene, a larger pore titanium zeolite such as a titanium zeolite having a structure isomorphous with zeolite beta is preferred.

Particularly preferred titanium zeolites include the class of molecular sieves commonly called titanium silicalites, particularly TS-1 (which has a topology similar to ZSM-5), TS-2 (which has a topology similar to ZSM-11), and TS-3. Also suitable are titanium zeolites that have framework structures isomorphous to zeolite beta, mordenite, ZSM-48, ZSM-12, and MCM-41. Preferred titanium zeolites contain no elements other than titanium, silicon, and oxygen in the lattice framework, although minor amounts of boron, iron, aluminum, or the like may be present. Titanium silicalites, such as TS-1, are most preferred. TS-1 can be made by any known method. See, e.g., U.S. Pat. No. 4,410,501, the teachings of which are incorporated herein by reference, and *J. Chem. Soc. Chem. Commun.* (1995) 155.

The titanium zeolites are preferably encapsulated within a vinylpyridine polymer. By "encapsulated," we mean that the zeolite particles are contained within and are surrounded by a thin layer of the polymer. Thus, encapsulation involves entrapping the zeolite particle within a polymeric coating. To interact with the titanium atoms, reactants must penetrate the vinylpyridine polymer coating.

The catalyst can be a simple admixture of the titanium zeolite and a vinylpyridine polymer. In this case, it is convenient to just mix titanium zeolite powder with the finely ground vinylpyridine polymer, preferably a crosslinked vinylpyridine polymer.

Vinylpyridine polymers suitable for use in making the polymer-encapsulated titanium zeolites are homopolymers or random and block copolymers produced by free-radical, ionic, or coordination polymerization of vinylpyridines and optional polymerizable comonomers. The polymers can be generated by bulk, solution, suspension, or emulsion polymerization methods. A variety of poly(4-vinylpyridine)s, poly(2-vinylpyridine)s and vinylpyridine copolymers are commercially available.

The polymers incorporate at least one vinylpyridine monomer. Suitable vinylpyridine monomers incorporate a pyridine or pyridine-like moiety. They include, for example, 2-vinylpyridine, 3-vinylpyridine, 4-vinylpyridine, 2-vinylquinoline, 4-vinylquinoline, 6-vinylquinoline, 2-vinylpyrazine, 2-vinylpyrimidine, 4-vinylpyrimidine, 4-vinyl-2,3-lutidine, 6-vinyl-2,3-lutidine, and the like, and mixtures thereof. 2-Vinylpyridine and 4-vinylpyridine are commercially available and are therefore particularly preferred.

The vinylpyridine monomer can be copolymerized with one or more ethylenic monomers, which can be hydrophilic, hydrophobic, or a combination of these. Suitable ethylenic monomers include, for example, vinyl aromatics, vinyl halides, vinyl ethers, vinyl esters, vinyl amides, ethylene, 1-olefins, unsaturated carboxylic acids, unsaturated anhydrides, cyclic unsaturated imides, acrylic acids, acrylate esters, allylic alcohols, dienes, and the like, and mixtures thereof. Vinyl aromatic monomers, especially styrene, are preferred. The ethylenic monomer can have pendant functional groups, as in, e.g., 4-(diphenylphosphino)styrene.

Preferred vinylpyridine polymers are crosslinked. A diacrylamide, divinylpyridine, divinylbenzene, or other diethylenic crosslinking agent can be included in the polymerization reaction to achieve the desired level of crosslinking (see, e.g., *J. Polym. Sci., C* 26 (1988) 347). Crosslinking can also be achieved by quaternizing the pyridine nitrogens with a difunctional crosslinker such as 1,4-dibromobutane, 1,6-dibromohexane, p-xylylene dichloride, or the like (see, e.g., *Makromol. Chem.* 177 (1976) 2295 and *J. Polym. Sci.* A-2 7 (1969) 1101). Poly(vinylpyridine)s that are 2% or 25% crosslinked are commercially available from Aldrich.

The vinylpyridine polymers preferably incorporate an antioxidant. The antioxidant can be an additive, such as a hindered phenol (BHT or the like). Alternatively, the antioxidant can be incorporated into the polymer chain by using a monomer that incorporates an antioxidant moiety, as in an acrylate ester of a hindered phenol (see, e.g., U.S. Pat. Nos. 3,953,402 and 4,690,995).

Generally, the amount of vinylpyridine monomer, optional ethylenic monomer, and optional crosslinking agent are controlled to provide a vinylpyridine polymer with desirable performance attributes. For example, preferred vinylpyridine polymers incorporate styrene or another hydrophobic comonomer to help keep the polymer from dissolving in aqueous oxidation reaction mixtures. Incorporating a crosslinking agent also usually limits water solubility. The vinylpyridine monomer is generally used in an amount needed to reduce or eliminate ring-opening side reactions in an olefin epoxidation process with hydrogen peroxide.

Catalysts of the invention can include a transition metal. The transition metal is needed for an epoxidation process that involves "in situ" generation of hydrogen peroxide. Suitable transition metals are found in Groups 7-11. The first row of these, for example, includes transition metals from Mn to Cu. Preferred transition metals are Re, Au, and the metals of Groups 8-10. Particularly preferred are Re, Fe, Ru, Co, Rh, Ir, Ni, Pd, Pt, Ag, and Au. The transition metal can be present in any suitable form as long as it is capable of catalyzing the reaction between hydrogen and oxygen gases to make hydrogen peroxide. For example, it may be present as the free metal (e.g., Pt or Pd metal), as a mixture of metals (e.g., Pd—Au, Pd—Pt, or the like), or it may be part of a complex that incorporates the metal or metals and other ligands (e.g., $PtCl_2$, $Pd(NH_3)_4Cl_2$, tris(benzylideneacetone) dipalladium(0), or tetrakis(triphenyl-phosphine)palladium (0)). The transition metal or transition metal complex can be supported on silicas, aluminas, carbons, zeolites (e.g., titanium silicalites), clays, organic polymers such as crosslinked polystyrene, or any other conventional support prior to being encapsulated within or combined with a vinylpyridine polymer. Other examples of transition metal sources suitable for use include Pd/C, Pt/C, Pd/silica, Pd/alumina, Pd/silicalite, Pd/Y-zeolite, Pd/kaolin, Pd/ZSM-5, Pd on TS-1, Pt on TS-1, Pd—Pt on TS-1, $PdCl_2$, $PtCl_2$, $Pd(NH_3)_2Cl_2$, $PdBr_2$, $Pd(NO_3)_2$, palladium(II) acetate, tetrakis(acetonitrile)palladium(II) bis(tetrafluoroborate), tetrakis(aceto-nitrile)palladium(II) bis(hexafluorophosphate), $HAuCl_4$, $Au_2O_3$, $RhCl_3$, $IrCl_3$, and the like. In preferred catalysts of the invention, the transition metal is encapsulated within the vinylpyridine polymer.

There are many suitable ways to encapsulate titanium zeolites (and optionally, the transition metal) within a vinylpyridine polymer. Some of these techniques have been used to encapsulate pharmaceuticals to mask taste, impart storage stability, or target drug delivery; others have been used to encapsulate solid pesticide particles. Suitable techniques include, for example, spray-drying, spray-chilling, spray-coating, phase separation and coascervation, injection treatment coating, fluid bed coating, dry-on-dry coating, melt extrusion, vapor deposition, in-situ polymerization, including in-situ interfacial polymerization, and the like. These and other microencapsulation techniques are described in the introductory chapter of *Microcapsules and Nanoparticles in Medicine and Pharmacy*, M. Donbrow, Ed., pp. 1-14, and references cited therein, and in G. Beestman, "Microencapsulation of Solid Particles," *Controlled-Release Delivery Systems for Pesticides* (1999), H. Scher, Ed., pp. 31-54. See also U.S. Pat. No. 6,156,245.

Polymer encapsulation by phase separation/coascervation is one preferred technique. A suitable approach is illustrated by Kobayashi et al. (see *Chem. Commun.* (2003) 449 and references cited therein; *Angew. Chem., Int. Ed.* 40 (2001) 3469; *J. Am. Chem. Soc.* 120 (1998) 2985) with polystyrene as the polymer encapsulant. See also *Zairo Giiutsu* 3 (1985) 29, and *J. Appl. Polym. Sci.* 89 (2003) 1966.

In a particularly convenient coascervation approach, a modified version of the method of Kobayashi, a vinylpyridine-styrene copolymer is dissolved in tetrahydrofuran. Titanium zeolite is suspended in the mixture. Hexane is added to the suspension to induce precipitation of a polymer-encapsulated TS-1 (see Examples B and C, below). In another variation, the zeolite suspension in THF is prepared the same way, but hexane is not added. Instead, THF is allowed to evaporate slowly from the mixture, which allows phase separation and capsule formation to occur. The resulting microcapsules can then be isolated and dried (see Example A).

In-situ polymerization is another preferred technique. The titanium zeolite is suspended in a reaction medium containing a vinylpyridine, optional comonomer(s), an initiator, and other components, and polymerization proceeds to give the vinylpyridine polymer-encapsulated titanium zeolite. Suitable techniques include bulk, emulsion, suspension, and interfacial polymerizations.

In another in-situ polymerization example, a vinylpyridine or a mixture of a vinylpyridine and other ethylenic monomer(s) is polymerized in an aqueous suspension according to well-known techniques in the presence of a suspended titanium zeolite. The resulting polymer beads incorporate encapsulated titanium zeolite and are suitable for use as an oxidation catalyst.

The vinylpyridine polymer can incorporate recurring units of a fluorinated monomer. Particularly suitable are fluorinated monomers made by reacting fluorinated alcohols with acrylic ester precursors. These and other suitable fluorinated monomers have been described previously (see *Chem. Commun.* (2002) 788; *Tetrahedron* 58 (2002) 3889, *Org. Letters* 2 (2000) 393, *Polym. Degrad. Stab.* 67 (2000) 461; and *Chem. Commun.* (2000) 839.) For example, polymerization of trifluoroethylmethacrylate (from methacryloyl chloride and trifluoroethanol) with styrene and a vinylpyridine gives a fluorinated terpolymer. Polymer encapsulation can be effected either in-situ or later by phase separation/coascervation.

Catalysts comprising a titanium zeolite and a vinylpyridine polymer are valuable for catalyzing organic reactions, particularly ones that are hindered by trace levels of acidity. The epoxidation of propylene with hydrogen peroxide and TS-1 is exemplary.

The invention includes a process comprising epoxidizing an olefin in the presence of a catalyst which comprises a vinylpyridine polymer and a titanium zeolite. Suitable conditions for performing olefin epoxidations have been reported (see, e.g., *Appl. Catal. A* 221 (2001) 63 and *Sci. Tech. Catal.* (1994) 31) and are otherwise well known to those skilled in the art. Suitable olefins include, for example, ethylene, propylene, butenes, 1-hexene, 1-octene, styrene, and the like, and mixtures thereof. Propylene is preferred.

Optionally, the epoxidation process is performed in the presence of a solvent. The choice of solvent will depend on many factors, including the solubilities of the reactants and products, the reaction conditions, the type of equipment, and other factors. Suitable solvents include, for example, water, alcohols, water/alcohol mixtures, oxygenated hydrocarbons (esters, ketones, ethers, or the like), aliphatic and aromatic hydrocarbons, liquid or supercritical carbon dioxide, and the like, and mixtures thereof. Preferred solvents are water, alcohols, carbon dioxide, and mixtures thereof. Aqueous methanol is particularly preferred.

In a preferred epoxidation process, the olefin is propylene and the epoxide is propylene oxide. Suitable procedures and reaction conditions for making propylene oxide from propylene with titanium zeolites and hydrogen peroxide have been described previously; see, e.g., U.S. Pat. Nos. 6,037,484 and 6,194,591, the teachings of which are incorporated herein by reference. If desired, the hydrogen peroxide can be generated "in situ" from gaseous hydrogen and oxygen in the presence of a transition metal (see, e.g., U.S. Pat. No. 6,403,815). The epoxidations are preferably performed at a temperature within the range of about 10° C. to about 100° C., more preferably from about 40° C. to about 80° C., and most preferably from about 50° C. to about 70° C.

Surprisingly, the presence of a vinylpyridine polymer enhances the catalyst's ability to selectively produce propylene oxide from propylene and $H_2O_2$ with a minimal proportion of ring-opening products such as propylene glycol and propylene glycol ethers (see Examples 1-10, Comparative Examples 11-12, and Table 1, below). In particular, when the titanium zeolite is encapsulated within a thin layer of the polymer (Examples 1-7), selectivity to PO improves dramatically at 50° C. from 91% to 99% PO/POE (where PO/POE is the molar ratio of PO to PO equivalents; moles of "PO equivalents"=moles of PO+moles of PO-based glycols and glycol ethers). In other words, the ring opening side reactions are almost completely suppressed! Preferably, the PO/POE ratio is greater than 95%; more preferably, the PO/POE ratio is greater than 98%. As Examples 8-10 demonstrate, a more modest yet valuable increase in selectivity results from using a simple admixture of a crosslinked vinylpyridine polymer and TS-1 (to about 96% PO/POE at 50° C.).

Interestingly, the benefits of including a vinylpyridine polymer extend to reactions at elevated temperature, thereby expanding the useful temperature range for the process. With TS-1 alone, ring opening becomes debilitating at 70° C.; the molar PO/POE is only about 82% (see Comparative Example 12). Admixing the TS-1 with a crosslinked vinylpyridine polymer (Example 10) improves the selectivity to about 94%. Results are even better when the vinylpyridine polymer encapsulates the TS-1 (see Examples 5-7; PO/POE=96-99%).

The use of a vinylpyridine polymer provides a way to keep the pyridine moiety in the reactor, even if the process is operated continuously. Soluble pyridines, in contrast (see U.S. Pat. No. 6,037,484), need to be replenished in a continuous process.

Vinylpyridine polymer-encapsulation of titanium zeolites provides additional advantages. First, polymer encapsulation makes it easy to recover the titanium zeolites. When used in powder form, titanium zeolites can blind filters or migrate undesirably in a reaction system. While this is remedied by converting the titanium zeolite to a pellet or by spray drying it to increase particle size, such techniques are costly. Polymer encapsulation makes the titanium zeolite easy to recover by ordinary filtration methods. Moreover, recovered vinylpyridine polymer-encapsulated titanium zeolites can often be used without further processing.

The invention includes a process for making hydrogen peroxide. The process comprises reacting hydrogen and oxygen in a solvent in the presence of a catalyst comprising a vinylpyridine polymer-encapsulated transition metal to produce hydrogen peroxide. Suitable vinylpyridine polymers, transition metals, and encapsulation methods have already been described herein. Suitable solvents and reaction conditions for making hydrogen peroxide have been described previously (see copending application Ser. No. 10/796,810, filed Mar. 9, 2004, the teachings of which are incorporated herein by reference).

The following examples merely illustrate the invention. Those skilled in the art will recognize many variations that are within the spirit of the invention and scope of the claims.

EXAMPLE A

Preparation of Poly(4-vinylpyridine-co-styrene)-Encapsulated TS-1

Styrene (10 g) and 4-vinylpyridine (10 g) are dissolved in tetrahydrofuran (THF, 200 mL) in a glass reactor. 2,2'-Azobisisobutyronitrile (AIBN, 0.2 g) is added, and the stirred mixture is degassed with nitrogen and is heated to 80° C. and held there for about 6 h. The reactor is cooled and the contents are removed. Hexane is added to precipitate the polymer. Yield of light pink powder: 14.4 g. $M_n$: 5200; $M_w$: 9200; $M_w/M_n$: 1.76. The polymer contains about 62 mole % of 4-vinylpyridine units.

A sample of the copolymer (2.5 g) is dissolved in THF (10 g) at room temperature. TS-1 (2.5 g) is added, and the mixture is stirred at room temperature. As THF slowly evaporates, the mixture thickens. The viscous mixture is transferred to a vacuum oven and remaining volatiles are removed at 60° C. The residue is then ground to a fine yellow powder.

EXAMPLE B

Preparation of Poly(4-vinylpyridine-co-styrene)-Encapsulated TS-1

A sample of poly(4-vinylpyridine-co-styrene) prepared in Example A (1.0 g) is dissolved in THF (3.0 g). Spray-dried TS-1 (1.18 g; contains 15-20 wt. % silica as a binder) is added to give a slurry. Hexane is added to induce precipitation of the polymer. The resulting polymer-encapsulated product is collected by filtration, dried under vacuum at 60° C., and ground to a fine powder. Yield: 2.0 g.

EXAMPLE C

Preparation of Poly(2-vinylpyridine-co-styrene)-Encapsulated TS-1

Poly(2-vinylpyridine-co-styrene) (Aldrich, $M_n$=130,000, 2.0 g) is dissolved in THF (10 g). Spray-dried TS-1 (2.07 g) is added to give a slurry. Hexane is added to induce precipitation of the polymer. The resulting polymer-encapsulated product is collected by filtration, dried under vacuum at 60° C., and ground to a fine powder.

EXAMPLE D

Preparation of Admixed TS-1 and Crosslinked Poly(4-vinylpyridine)

TS-1 from Comparative Example E (150 mg) is admixed with crosslinked poly(4-vinylpyridine) (Aldrich, 2% crosslinked, 300 mg) to give a homogeneous powder.

COMPARATIVE EXAMPLE E

Preparation of TS-1

A sample of TS-1 obtained from Chemical National Labs of India, a powder of about 0.2 microns, is calcined at 550° C. to remove the template. It contains 2.2 wt. % Ti.

Propylene Epoxidations

EXAMPLES 1-10 and COMPARATIVE EXAMPLES 11-12

A 100-mL Parr reactor is charged with a 70:25:5 wt. % solution of methanol/water/hydrogen peroxide (40 g) and one of Catalysts A-D (Examples 1-10) or Catalyst E (Comparative Examples 11 and 12) as shown in Table 1. The reactor is sealed and charged with propylene (20-23 g). The magnetically stirred reaction mixture is heated at the desired reaction temperature (50, 60 or 70° C.) for the time indicated in Table 1 (0.5 to 2.0 h), and is then cooled to 10° C. The liquid and gas phases are analyzed by gas chromatography. Results appear in Table 1.

The preceding examples are meant only as illustrations. The following claims define the invention.

TABLE 1

Propylene Epoxidations

| Ex | Cat | Description[1] | Amt.[2] (mg) | Time (h) | Temp. (° C.) | $H_2O_2$ % conv. | PO mmol | PO/POE[3] (%) |
|---|---|---|---|---|---|---|---|---|
| 1 | A | poly(4-VP-sty)-encap TS-1 | 300 | 0.5 | 50 | 34.6 | 16.4 | 99.2 |
| 2 | A | | 300 | 1.0 | 50 | 50.2 | 24.7 | 99.3 |
| 3 | A | | 400 | 2.0 | 50 | 78.2 | 37.3 | 99.1 |
| 4 | A | | 300 | 1.0 | 60 | 69.9 | 33.0 | 99.0 |
| 5 | A | | 300 | 0.5 | 70 | 69.4 | 32.7 | 98.9 |
| 6 | B | poly(4-VP-sty)-encap spray-dried TS-1 | 326 | 0.5 | 70 | 89.5 | 42.8 | 97.9 |
| 7 | C | poly(2-VP-sty)-encap spray-dried TS-1 | 352 | 0.5 | 70 | 94.0 | 43.8 | 96.1 |
| 8 | D | Admixed TS-1 + crosslinked poly(4-VP) | 450 | 0.5 | 50 | 79.2 | 36.2 | 95.5 |
| 9 | D | | 450 | 0.5 | 50 | 77.5 | 35.8 | 95.9 |
| 10 | D | | 450 | 0.5 | 70 | 97.8 | 44.3 | 93.5 |
| C11 | E | TS-1 | 150 | 0.5 | 50 | 68.5 | 37.2 | 91.0 |
| C12 | E | | 150 | 0.5 | 70 | 97.3 | 41.2 | 82.4 |

[1]Polymer-encapsulated catalysts are 1:1 TS-1 to polymer by weight.
[2]All runs used 150 mg of TS-1 except Ex 3 (200 mg).
[3]Calculated from moles of PO/(moles of PO + moles of PG + moles of PG ethers) × 100.

I claim:

1. A catalyst comprising a vinylpyridine polymer and a titanium zeolite.

2. The catalyst of claim 1 wherein the titanium zeolite is encapsulated within the vinylpyridine polymer.

3. The catalyst of claim 2 wherein the titanium zeolite is TS-1.

4. The catalyst of claim 2 wherein the vinylpyridine polymer is a copolymer of a vinylpyridine and styrene.

5. The catalyst of claim 1 further comprising a transition metal.

6. The catalyst of claim 5 wherein the transition metal is palladium.

7. The catalyst of claim 1 comprising an admixture of the vinylpyridine polymer and the titanium zeolite.

8. The catalyst of claim 1 wherein the vinylpyridine polymer is crosslinked.

9. A process which comprises epoxidizing an olefin in the presence of hydrogen, oxygen, and the catalyst of claim 5.

10. The process of claim 9 wherein the olefin is propylene and the transition metal is palladium.

* * * * *